United States Patent [19]

Mifflin

[11] Patent Number: 4,911,910

[45] Date of Patent: Mar. 27, 1990

[54] PURIFIED EQUINE IMMUNOLOGLOBULINS AND METHOD OF USE THEREOF

[75] Inventor: Raymond E. Mifflin, Germantown, Md.

[73] Assignee: Biotech Research Labs, Inc., Rockville, Md.

[21] Appl. No.: 934,838

[22] Filed: Nov. 25, 1986

[51] Int. Cl.$^4$ .................. C07K 15/06; A61K 39/395; A61K 39/40; A61K 35/16

[52] U.S. Cl. ..................... 424/85.8; 424/88; 424/101; 530/387; 530/416

[58] Field of Search ................. 424/85, 88, 101, 85.8; 530/416, 387; 435/68

[56] References Cited

U.S. PATENT DOCUMENTS

| | | | |
|---|---|---|---|
| 3,664,994 | 5/1972 | Perper | 424/85 |
| 4,136,094 | 1/1979 | Condie | 530/387 |
| 4,186,192 | 1/1980 | Lundblad et al. | 424/85.8 |
| 4,272,521 | 6/1981 | Zuffi | 530/387 |
| 4,434,093 | 2/1984 | Zolton et al. | 530/387 |
| 4,639,513 | 1/1987 | Hou et al. | 530/387 |
| 4,675,384 | 6/1987 | Dromard et al. | 530/416 |

OTHER PUBLICATIONS

Hardy, The Influence of Specific Chemical Factors in the Solvent on the Absorption, Etc., J. Physiol., 204:607–632 (1969).

Jeffcott, Passive Immunity and Its Transfer with Special Reference to the Horse, Biol. Rev., 47:439–64 (1977).

P. C. Montgomery, Molecular Aspects of Equine Antibodies; Proc. 3d. Int. Conf. Equine Infectious Diseases 343–363 (1973).

Wernet et al., cited in Chem. Abstracts, vol. 82:123213x, 1975.

Nielsen et al., cited in Biol. Abstracts 81:23731, 1986 (Feb. 1).

Steinbuch et al., cited in Chem. Abstracts Vol. 74:30365t.

*Primary Examiner*—Jacqueline M. Stone
*Attorney, Agent, or Firm*—Iver P. Cooper

[57] ABSTRACT

Equine immunoglobulins are recovered from the pass-through fraction of a QAE column loaded with equine serum in an acidic buffer. The recovered antibodies are electrophoretically free of non-immunoglobulin proteins, including transferrin, and are recovered in a higher yield than with known methods. The purified immunoglobulins may be used to treat failure of passive transfer of maternal immunity to foals.

9 Claims, 2 Drawing Sheets

PURIFIED EQUINE IMMUNOLOGLOBULINS AND METHOD OF USE THEREOF

BACKGROUND OF THE INVENTION

This invention relates to a mixture of purified equine immunoglobulins suitable for use in treating failure of passive transfer in foals, and essentially free of non-immunoglobulin proteins, and to the methods of preparing and using it.

The newborn foal is very susceptible to infection immediately after birth. In nature, the foal is normally given protection by its mother's first milk, or colostrum, which is rich in maternal antibodies. The foal absorbs these antibodies during its first 24 hours of life. Afterward, the villous epithelial cells of the small intestine undergo changes which frustrate further adsorption of immunoglobulins.

Unfortunately, foals which are born too weak to nurse or which are rejected by their mothers after birth become immunodeficient. A complete or partial failure of passive transfer of immunity may also arise through premature lactation by the mare, abnormally low immunoglobulin content in the mare's colostrum, or abnormally poor absorption of immunoglobins by the foal. See Liu, Systemic Diseases of the Newborn Foal, Vet. Clinics of North Amer.: Large Animal Practice, 2: 361 (1980)

The treatment of failure of passive transfer in newborn animals by administration of colostrum milk or salt-purified Ig serum fractions is known. See Newson, U.S. No. 4,096,244; Line, U.S. No. 2,607,716; Heinbach, U.S. No. 3,128,230; Michaelson, U.S. No. 3,646,193; Khours, U.S. No. 3,984,539; Divers, et al., Am. Ass'n Equine Practitioners Proceedings, 473 (1982); Burton, et al., Am. J. Vet. Res., 42: 308 (1981); Le Blanc and Asbury, Equine Vet. Sci., 5: 78 (1983). Commercial preparations exist, notably FOAL IMMUNE (Lake Immunogenetics, 345 Berg Road, Ontario, N.Y. 14519) and EQUIGAM (Equigam Products, Inc., 1615 West Waters Ave., Tampa, Fla. 33604) which are merely sterile whole serum, containing antibodies. These crude preparations have numerous disadvantages, including short shelf lives, low immunologic potency, and contamination with antigenic or pyrogenic substances.

Perper, U.S. No. 3,664,994 used DEAE-dextran chromatography at pH 7.2-7.85 to separate equine immunoglobulins from serum. Procedurally, his method differed from that described herein in several respects: (1) use of DEAE rather than QAE; (2) use of a basic rather than an acidic buffer; and (3) retention rather than pass through of the antibodies. We have found that equine immunoglobulins, unlike human immunoglobulins, respond adversely to basic conditions. Our product also differs significantly from that of Perper, in that, to obtain an alleged pure equine Ig fraction, Perper limited himself to a recovery of 50 mg of protein from 25 ml of serum. It is believed that Perper's fractions do not contain all of the important equine antibodies, particularly anti-tetanus IgG-T, which is known to be difficult to purify. See Kent and Blackmore, Equine Vet. J. 17(2): 119-124 (1985). Perper was interested only in horse anti-lymphocyte gamma globulin, not in horse antibodies generally. We also believe that Perper's fractions may have been contaminated with transferrin, in view of our own experience with DEAE chromatography, as well as the reference to transferrin contamination in the manufacturer's literature regarding the use of Zetaprep-15 DEAE disks. It has been postulated that transferrin plays a role in iron toxemia in foals.

It is conventional in the art to purify immunoglobulins from sera by DEAE chromatography under basic conditions. See U.S. No. 4,541,953; U.S. No. 4,562,160; U.S. No. 4,331,649. Surprisingly, we discovered that use of such conditions in purifying equine Ig resulted in precipitation of the antibodies, followed by aggregate formation, when the product was concentrated or stored at 4° C.

Equine antibodies have been studied to some degree. See Montgomery, Proc 3d Int. Conf. Equine Infectious Disease, Paris, 1972, at 343-63 (1973); McGuire, et al., Id., 364-81 (1973).

The major equine blood proteins are transferrin (a 90K beta-globulin), albumin, prealbumin, the XK protein family, hemoglobin and various enzymes. Braend, Id, 394-406 (1973). A purified Ig fraction should be free of these proteins.

SUMMARY OF THE INVENTION

We have found that conventional approaches to the purification of equine immunoglobulins, particularly, IgG, are unsatisfactory. The ethanol precipitation method gave a yield of only 63% and even then the product was contaminated with transferrin and albumin. Similar problems were experienced with ammonium sulfate and octanoic acid precipitations. We also experimented with DEAE ion exchange chromatography. Here, the support had only a 20% capacity for the horse IgG, transferrin was a major contaminant of the product, and large buffer volumes were needed for elution or resuspension of the IgG.

When we switched to a QAE chemistry, we continued to experience precipitation problems. Attempts to overcome this problem by providing 0.05M NaCl or 4% lactose in the buffer was unsuccessful. However, we succeeded in obtaining a greater than 90% recovery of IgG when we used a pH of 6.3 and a salt concentrated of 0.015M NaCl, which, in 0.013M phosphate, is our preferred equilibration buffer. The equine Ig fraction thus obtained was essentially free of non-immunoglobulins, including transferrin, and contained antibodies against tetanus, eastern, western and Venezuelan encephalomyelitis, equine influenza, rhinopneumonitis, and strangles.

BRIEF DESCRIPTION OF THE DRAWINGS

FIG. 1 demonstrates the absence of any contaminants including transferrin which as discussed previously usually coelutes with the IgG fraction.

FIG. 2 demonstrates the presence of major contaminating proteins including albumin and transferrin when using the other accepted methods which included DEAE as suggested by Perper. In lane 2 the pattern is very near that of serum, i.e. there is a series of contaminating proteins. In lanes 3 and 5 the same pattern is repeated again demonstrating the inefficiency of the labeled methods. Lane 6 is nearly the same as the previous lanes with the exception that less albumin is present. Lanes 7 and 8 are nearly equivalent in that transferrin is the major contaminant.

DETAILED DESCRIPTION OF THE INVENTION

Example 1: Purification of IgG

Figure 1:
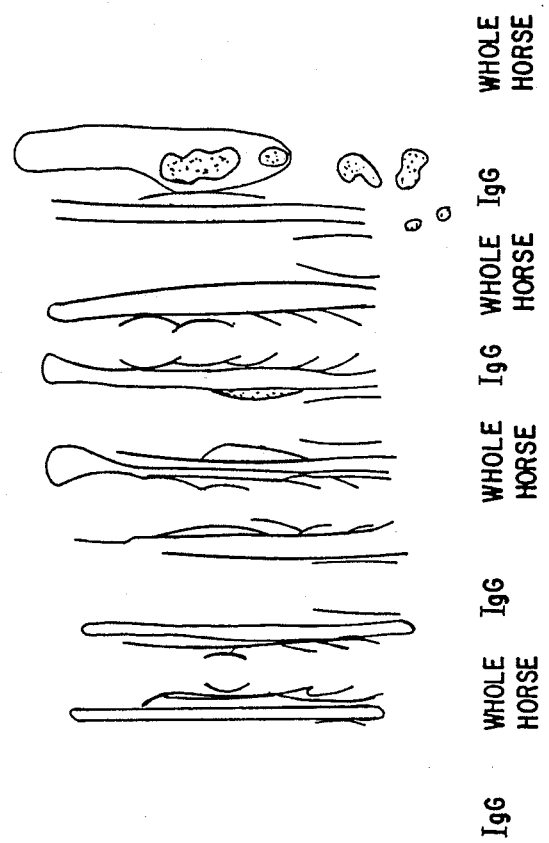
FIG. 1 is a comparison of the immunoelectropherograms of the purified IgG hereof with whole horse serum.

The horses that are used as our serum source have been immunized with a variety of vaccines including the Jen-Sal four way vaccine (Jensen-Salsberg Laboratories Division of Burroughs Wellcome Co. Kansas City, Miss. 64141; contains Eastern, Western, Venezuelan Encephalomyelitis and Tetanus antigens). The other vaccines contained antigens for Equine Influenza, Equine Rhinoipneumonitis, Strangles, Rabies and Equine Herpes Virus I (Mares). Other antigens that horses are commonly exposed to in the environment include organisms such as *Streptococcus zooepidemicus, Streptococcus equi, Escherichia coli, Pseudomonas aeruginosa, Klebsiella pneumoniae,* Corynebacterium Spp., Proteus Spp., Staphylococcus Spp., alpha-hemolytic Streptococci, Enterobacter Spp., *Staphloccus epidermidis,* and *Actinobacillis equi.* Mares may also be exposed to yeasts such as Candida Spp. and rarely Aspergillus Spp. Of course, the horses may be immunized with other antigens to obtain a desired "mix" of antibodies.

Sera from these immunized horses was then subjected to the following purification procedure:

1. Rinse and equilibrate Zetaprep QAE cartridges (Cuno) with 0.013M phosphate buffer pH 6.3. When pH of discharge is equal to starting buffer, the columns are ready for use. It is best to take 3-4 samples at intervals after pH is observed in order to be sure the column is equilibrated.

2. Dilute serum 1:15 with 0.013M phosphate buffer, pH 6.3, conductivity less than 2.0 mMhos.

3. Apply to columns at a suitable flow rate, such as 2-4 L/min for 2-3 minutes (column residence time). Start collecting samples immediately since the IgG is present in the pass through fraction and the other proteins are bound to the QAE. This includes transferrin which tends to coelute with IgG using other purification methods.

4. After the serum has been applied, it is rinsed with 0.013M phosphate buffer pH 6.3 and collected.

5. Sodium chloride is added to elute. Elute the non-Ig proteins so the column may be reused. The IgG is then concentrated using ultrafiltration and the ultrafiltrate is then lyophilized. The water used for the experiments is pyrogen free.

The IgG is analyzed using radial immunodiffusion, immunoelectrophoresis, SDS-PAGE, or ELISA (see below).

Example 2: Characterization of IgG Fraction

A. Radial Immunodiffusion (RID)

The technique of single radial immunodiffusion (RID) is the most widely used methods for quantitative determination of classes of immunoglobulins and other serum and plasma proteins. This technique combines rapid and easy sample application with a high degree of accuracy and reproducibility.

The method is derived primarily from the works of Fahey, and of Mancini. Antiserum specific for the protein to be measured is incorporated into agarose gel. The sample antigen diffuses into the gel containing the antibody, and a ring of precipitation forms that is proportional in size to the concentration of the antigen. A linear relationship exists between the diameter when plotted on semi-log graph paper. This method is time and temperature dependent.

RID was conducted using a kit supplied by VMRD, Inc. (P.O. Box 502, Pullman, Wash. 99163), and the kit was used in accordance with the manufacturer's instructions. The kit contains prepoured plates which contain monospecific horse antisera for the quantitation of both total IgG and IgG(T). Sharp, easy to read precipitin rings were visible in less than 24 hours.

Table I (below) shows the analysis of 11 purification runs.

TABLE I

| Total Serum IgG | Total IgG (Purified) | Serum IgG (T) | IgG CONCENTRATION (mg/ml) (Radial Immunodiffusion) | | |
|---|---|---|---|---|---|
| | | | Total IgG (T) (Purified) | % Recovery IgG (T) | % Recovery IgG |
| 16.0 | 15.5 | .63 | .65 | 96.9 | 96.9 |
| 18.5 | 17.0 | .22 | .23 | 95.6 | 91.9 |
| 27.3 | 25.0 | .33 | .38 | 87.0 | 91.6 |
| 19.5 | 18.0 | .37 | .40 | 92.5 | 92.3 |
| 19.0 | 18.0 | .45 | .49 | 91.8 | 94.7 |
| 19.5 | 18.0 | .48 | .51 | 94.1 | 92.3 |
| 19.3 | 18.0 | .50 | .53 | 94.3 | 93.3 |
| 25.5 | 24.8 | .60 | .61 | 98.4 | 97.3 |
| 41.0 | 40.0 | .18 | .20 | 90.0 | 97.6 |
| 14.0 | 13.0 | .50 | .53 | 94.3 | 92.9 |
| 19.6 | 18.0 | .30 | .31 | 96.7 | 91.8 |

By way of comparison, Equigam contained 2-2.2 mg/ml of total IgG and less than 0.05 mg/ml of IgG(T). Thus, the product of the present invention contained 10-20 times more antibody than does a current commercial product.

Moreover, my recovery of IgG and IgG(T) exceeded 85%. I believe that no prior method provides a recovery exceeding even 65%.

B. Immunoelectrophoresis

A horse IgG sample, purified horse IgG solution, and a standard horse serum, each mixed with bromophenol blue in a barbital/EDTA buffer, are placed in the antigen wells and electrophoresed for 40 min on a Corning Electrotrace Immunoelectrophoresis agarose film gel. Goat anti-horse serum and Anti Whole Horse Serum are added to different antibody troughs on the gel and antigen and antibody are allowed to diffuse for 18 hours at room temperature. The precipitin lines are stained by immersing the gel in amido black.

Figure 2:
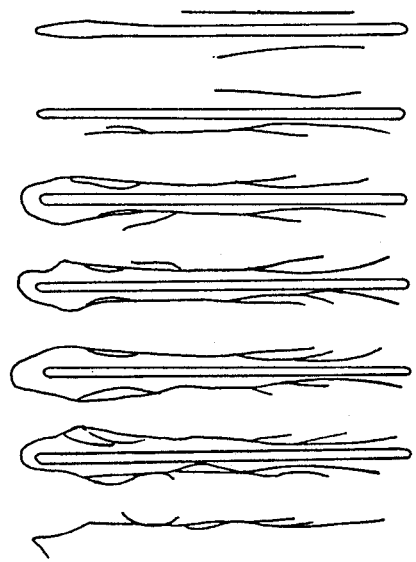
FIG. 2 is a comparison of the immunoelectropherograms of whole horse serum (lane 1) with that of EtOH pptn. (lane 2), ammonium sulfate pptn. (lanes 3-5), octanoic acid pptn. (lane 6) DEAE chromatography (lane 7) and EtOH pptn. (lane 8).

The immunoelectrophoretic pattern of the equine Ig fraction purified by the present method demonstrates the presence of one component of whole horse serum and the absence of other components (FIG. 1). The products of conventional purification methods are more heterogeneous (FIG. 2).

C. SDS-PAGE

Electrophoresis was performed according to the method of Laemmli, Nature, 227: 689 (1970) on 12.5% SDS-PAGE for 4.0 hours at 10 mA for 30 minutes, then 25 mA until tracking dye (Pyronin Y) moves 10 to 15 cm. Each sample produces two distinct bands which correlates to the light and heavy chains of the IgG molecule with no contaminants visualized.

D. Elisa

To prepare samples for analysis, dissolve 40 mg of each sample in 10 ml of Phosphate buffered saline. Each plate receives JEN-SAL vaccine 1:10 in 0.1M $Na_2CO_3$. Mix well. Add 0.1 ml of diluted vaccine to each well of 96 well ELISA plate, seal plate with plastic plate sealers and incubate at 4° C. overnight, after incubation shake excess vaccine off plates. Wash the plate twice with PBS-Tween 20. After washing add 0.1 ml 2% BSA in PBS, incubate 30 minutes at 37° C. or 1 hour at room temperature. After incubation wash plate×2 with PBS-Tween. Dry the plates at room temperature, seal the plates, and store them at 4° C. until ready for use.

In testing for IgG, to each well add 0.1 ml of 1% BSA in PBS-Tween 20. Weigh out 40 mg of horse IgG to be tested, add 10 ml of PBS. Vortex until dissolved. Dilute from 1/10 to 1/41,960 in serial dilutions of 1:2 with 1% BSA-Tween. Mix each dilution thoroughly. After dilutions are made add 0.1 ml to each well as marked, one row will be 1% BSA in Tween 20. Incubate plates 30 minutes at 37° C., after incubation shake horse IgG off plate. Wash twice with PBS-Tween 20. Add 0.1 ml of peroxidase labeled goat anti horse IgG diluted in 1% BSA-PBS Tween (each goat anti horse IgG lot must be pretested for correct dilution as each lot varies from manufacturer) to each well except the wells containing diluent only. Add 0.1 ml 1% BSA-PBS Tween 20 to each well. Incubate at 37° C. for 30 minutes. After incubation, wash twice with PBS-Tween 20. Add 0.1 ml TMB substrate (made by adding 4 ml TMB buffer to 10 ml citrate buffer) to each well. Incubate at room temperature for 15 minutes. Add 0.05 ml 2M $H_2SO_4$ to each well. After color develops read $A_{450}$ sample and $A_{570}$ reference in Dynatech plate reader. Determine mean $A_{450}$. Calculate titer.

The ELISA developed for the activity assay uses the Jen-Sal four way vaccine as the antigen source. The specific activity of my preparation is 0.015 mg/ml compared to 0.062 mg/ml of Equigam. That is it would take 4 times the amount of Equigam to obtain the same activity as that of my purified IgG. The amount of active material in Equigam is less than 2 micrograms/ml as opposed to 15 micrograms/ml of the product of the present invention.

While, as described above, the equine immunoglobulins were purified from serum, other biological fluids containing Ig's, such as colostrum, may be used as source materials. However, serum is preferred because it is inexpensive and readily obtained.

The preferred pH for the ion exchange chromatography step is 6.3. Some variation in the pH, such as from pH 6.2-6.4, is unlikely to adversely affect the process.

The following table shows the results of our systematic study of the effect of pH.

TABLE II

| pH EFFECTS | | |
|---|---|---|
| pH | Precipitate | Activity |
| 9.0 | None | None |
| 8.8 | None | None |
| 8.5 | None | None |
| 8.3 | None | None |
| 8.2 | None | + |
| 8.0 | + | + |
| 7.8 | + | + |
| 7.5 | + | + |
| 7.2 | +++ | + |
| 7.0 | ++ | + |
| 6.8 | ++ | ++ |
| 6.5 | ++ | ++ |
| 6.44 | Slight | +++ |
| 6.3 | None | ++++ |
| 5.9 | None | ++ |
| 5.65 | None | ++ |
| 5.47 | None | ++ |
| 5.14 | None | ++ |
| 5.0 | None | + |

TABLE II-continued

| pH EFFECTS | | |
|---|---|---|
| pH | Precipitate | Activity |
| 4.85 | None | Slight |
| 4.5 | None | Slight |
| 3.23 | None | None |
| 2.76 | None | None |
| 2.6 | None | None |
| 2.47 | None | None |

It is known that in sucking ungulates, gastric pH values usually vary between pH 3 and 5. See Bainter, INTESTINAL ABSORPTION OF MACROMOLECULES AND IMMUNE TRANSMISSION FROM MOTHER TO YOUNG 80 (1986).

Salt concentrations in the buffer are preferably below physiological levels, and most preferably is 0.015M NaCl.

Table III shows our experience with buffers of different salinities:

TABLE III

| EFFECT OF SALT CONCENTRATION | |
|---|---|
| Millimolar Concentration of Sodium Chloride | Osmotic Diarrhea |
| 0.5 | +++ |
| 0.4 | ++ |
| 0.3 | + |
| 0.25 | Slight |
| 0.2 | Slight |
| 0.15 | None |
| 0.10 | None |

While QAE is the preferred chromatographic column, other columns which pass through the immunoglobulins and retain the other proteins may be employed.

The preferred molarity of phosphate is 13 mM. However, phosphate levels may be at least as high as 0.02M.

The equine Ig fraction obtained by the purification method of this invention may be combined with polyclonal or monoclonal antibodies obtained by other means. These antibodies may be directed against particular natural or synthetic antigens.

Example III: Immunization with Purified IgG

In gathering data on the transfer of the antibody and the dosage level, I tried several combinations of reconstitution buffer as well as non-lyophilized preparation with various additives that would either stabilize the protein in solution or possibly prevent the destruction of the protein on exposure to the foal's gut. In order to stabilize the protein in solution I tried 30% w/v glycerol and 30% w/v of propylene glycol. The propylene glycol would be the additive of choice. The increase was not significant over the use of water for injection or phosphate buffer.

In order to promote transfer, we tried bovine trypsin inhibitor and soybean trypsin inhibitor. The soybean trypsin inhibitor increased absorption approximately 20 fold more than bovine trypsin inhibitor. Potassium isobutyrate is also effective for this purpose. The foals were all dosed by stomach intubation. The assay for determining IgG in the foal's blood was radial immunodiffusion.

The IgG fraction is preferably lyophilized for storage. However, if it is to be used shortly after purification it may be used directly. The lyophilized fraction retains essentially all the activity of the liquid form.

In use, the lyophilized, purified immunoglobulin fraction is reconstituted and administered to the foal, preferably by gastric intubation. It is desirable that the composition include an agent which promotes intestinal uptake of the immunoglobulin. This agent may be soybean trypsin inhibitor, but is preferably potassium isobutyrate.

In addition, the purified Ig fraction of this invention maybe used for purposes other than treatment of failure of passive transfer. Particularly, the prevention or treatment of endometritis. In this use the purified Ig is infused into the uterus.

I claim:

1. A purified equine IgG fraction, derived from equine blood, said fraction being essentially free of non-immunoglobulin protein including transferrin, and, said fraction being immunologically reactive with tetanus, encephalomyelitis, equine influenza, rhinopneumonitis and strangles antigens.

2. A purified equine IgG fraction derived from equine blood and retaining at least one immunological activity of said blood, said fraction being essentially free of non-immunoglobulin protein, including transferrin, derived from said blood, further comprising a propylene glycol stabilizer.

3. A purified equine IgG fraction derived from equine blood and retaining at least one immunological activity of said blood, said fraction being essentially free of non-immunoglobulin protein including transferrin, derived from said blood, further comprising an agent which promotes the intestinal uptake of antibody.

4. The fraction of claim 3 in which the agent is soybean trypsin inhibitor.

5. The fraction of claim 3 in which the agent is potassium isobutyrate.

6. A method of treating the failure of passive transfer in foals which comprises administering to a foal a purified equine immunoglobulin according to claim 1.

7. A method of treating the failure of passive transfer in foals which comprises administering to a foal a purified, immunologically active equine IgG fraction, and an effective amount of an agent which promotes intestinal uptake of IgG by foals.

8. The method of claim 7 in which the agent is soybean trypsin inhibitor.

9. The method of claim 7 in which the agent is potassium isobutyrate.

* * * * *

UNITED STATES PATENT AND TRADEMARK OFFICE
CERTIFICATE OF CORRECTION

PATENT NO. : 4,911,910　　　　　　　　　　　Page 1 of 2
DATED : March 27, 1990
INVENTOR(S) : MIFFLIN It is certified that error appears in the above-identified patent and that said Letters Patent is hereby corrected as shown below:

| | |
|---|---|
| In the Title, line 2 | Delete "IMMUNOLOGLOBULINS", insert therefor -- IMMUNOGLOBULINS -- |
| Inventor, line 1 | Delete "Germantown", insert therefor -- Rockville -- |
| Column 1, line 2 | Delete "IMMUNOLOGLOBULINS", insert therefor -- IMMUNOGLOBULINS -- |
| Column 2, line 38 | Delete "was", insert therefor -- were -- |
| Column 2, line 40 | Delete "concentrated", insert therefor -- concentration -- |
| Column 3, line 14 | Delete "Rhinoipneumonitis", insert therefor -- Rhinopneumonitis |
| Column 3, line 57 | Delete "methods", insert therefor -- method -- |
| Column 4, line 65 | Delete "Phosphate", insert therefor -- phosphate -- |

UNITED STATES PATENT AND TRADEMARK OFFICE
CERTIFICATE OF CORRECTION

PATENT NO. : 4,911,910

DATED : March 27, 1990

INVENTOR(S) : Mifflin

It is certified that error appears in the above-identified patent and that said Letters Patent is hereby corrected as shown below:

Column 4, line 68    Before "96", insert -- a --

Column 6, line 48    Delete "preparation", insert therefor -- preparations --

Signed and Sealed this

Twenty-first Day of July, 1992

Attest:

DOUGLAS B. COMER

Attesting Officer    Acting Commissioner of Patents and Trademarks